US005783450A

United States Patent [19]

Yoshida et al.

[11] Patent Number: 5,783,450
[45] Date of Patent: Jul. 21, 1998

[54] ANALYTICAL METHOD AND INSTRUMENT FOR ANALYSIS OF LIQUID SAMPLE BY LIQUID CHROMATOGRAPHY

[75] Inventors: Kasumi Yoshida, Mito; Junkichi Miura, Katsuta; Yoshio Fujii, Katsuta; Hiroshi Satake, Katsuta; Masahito Ito, Katsuta; Masao Kamahori, Hitachi, all of Japan

[73] Assignee: Hitachi, Ltd., Tokyo, Japan

[21] Appl. No.: 440,359

[22] Filed: May 12, 1995

Related U.S. Application Data

[63] Continuation of Ser. No. 96,272, Jul. 26, 1993, abandoned, which is a continuation of Ser. No. 597,412, Oct. 15, 1990, abandoned.

[30] Foreign Application Priority Data

Oct. 18, 1989 [JP] Japan .................................. 1-268945

[51] Int. Cl.$^6$ ...................................................... G01N 30/02
[52] U.S. Cl. ............... 436/161; 422/70; 422/82.08; 436/93; 436/111; 436/172; 436/177
[58] Field of Search ..................... 436/161, 93, 111, 436/177, 172; 422/70, 82.08; 210/198.2, 656; 73/61.55, 61.57, 61.56, 61.52

[56] References Cited

U.S. PATENT DOCUMENTS

| 3,918,913 | 11/1975 | Stevenson et al. | 422/70 |
| 4,224,278 | 9/1980 | Hogen Esch | 422/63 |
| 4,274,967 | 6/1981 | Snyder | 210/198.2 |
| 4,737,465 | 4/1988 | Bond et al. | 422/70 |
| 4,837,157 | 6/1989 | Turnell et al. | 422/70 |
| 4,913,821 | 4/1990 | Melcher | 436/161 |
| 5,011,608 | 4/1991 | Damjanovic | 210/656 |
| 5,093,267 | 3/1992 | Miura et al. | 210/656 |
| 5,277,871 | 1/1994 | Fujii et al. | 422/70 |

*Primary Examiner*—Jan Ludlow
*Attorney, Agent, or Firm*—Antonelli, Terry, Stout & Kraus, LLP

[57] ABSTRACT

A method and an instrument for separating and analyzing a very small quantity of constituents to be inspected contained in an analyte such as a class of catecholamines by liquid chromatography after labeling. The entire processes of analytical operations include principally three processes, a preparing process, an impurity elimination process and a separation process. When one sample is perceived, the sample is processed in these three processes. In this case, while one sample is being processed in an impurity elimination process, a sample preceeding the one sample is processed in a separation process, and a succeeding sample is processed in a preparing process. In other words, these three processes are performed essentially in parallel. With this, it is possible to remarkably reduce analysis time as compared with individual single sample analysis.

8 Claims, 10 Drawing Sheets

ANALYTICAL METHOD AND INSTRUMENT FOR ANALYSIS OF LIQUID SAMPLE BY LIQUID CHROMATOGRAPHY

This is a continuation of application Ser. No. 08/096,272, filed Jul. 26 1993, now abandoned, which is a continuation of Ser. No. 07/597,412 filed Oct. 15, 1990, now abandoned.

BACKGROUND OF THE INVENTION

The present invention relates to an analytical method and an instrument for analysis of a sample by liquid chromatography, and, more particularly, to an analytical method and an instrument for analysis suitable to enable performing an analytical operation of separating constituents with automatic preparing of the sample and utilizing liquid chromatography.

Liquid chromatography has a feature that, after separating constituents under a state of solution, an individual constituent can be analyzed selectively, and includes important analytical items in the field of clinical inspection, too. However, many of analytical means are complicated and take a long time for analysis, which prevents an increase in the number of analytes in an operation of a routine work such as clinical inspection in which a plurality of analytes have to be processed within a limited time and causes delay in popularization of automatic machines of this type.

Analysis of a class of catecholamines and analysis of prostaglandins may be mentioned as analytical items in which application to such a routine work lags behind. A class of catecholamines has been recognized to be effective in diagnosis of abnormality of cell tumor, circulatory organs, cranial nerve system, internal secretion metabolism and so forth and stress, and is being watched as an important item in the case of group examination for adult diseases. Further, prostaglandins show variegated physiological activities and have a plurality of types. Accordingly, it is necessary to separate respective constituents for determination.

When these analytical items are analyzed with separation by liquid chromatography, a sample and a luminescence label agent are made to react with each other and measurement is generally made with a fluorophotometer. As a labeling method, a prelabel method in which reaction with the label agent is made prior to separation of constituents by a separation column and a postlabel method in which reaction with the label agent is made after separation of constituents by a separation columns are known. In the postlabel method, however, detection with high sensitivity is difficult due to large diffusion of constituents after elution from the separation column, and the prelabel method is more advantageous when a minor constituent in a biological sample is measured.

In methods described, for example, in JP-A-61-88148 and JP-A-60-143766 a class of catecholamines is labeled (formed into a derivative) by a prelabel method and analyzed by chromatography.

In JP-A-61-88148, alumina is added to a sample so that catecholamines is adsorbed by alumina, and dansyl chloride is made to react during adsorption so as to form catecholamine into a derivative. Then, the sample formed into a derivative from alumina is desorbed and the liquid is concentrated by evaporation. The sample thus prepared is poured into a passage of liquid chromatograph so as to separate constituents and detect fluorescence.

Further, in JP-A-60-143766, after a formed sample such as blood plasma and urine is poured into the passage, catecholamine is labeled (formed into a derivative) while three types of reaction reagents are introduced into the passage one after another and made to flow in a reaction coil. After the sample thus processed is trapped and concentrated in a concentration column, the sample is transferred to the separation column, and constituents are separated and fluorescence is detected.

In methods described in, for example, JP-A-61-92599 and JP-A-58-108457 prostaglandins are labeled by the prelabel method and analyzed by chromatography.

More particularly, JP-A-61-92599 suggests a method in which a sample is labeled with fluorescence and constituents are separated with a separation column thereafter so as to measure with a fluorescence detector when prostaglandins are analyzed using said high speed liquid chromatography. Further details are not described in JP-A-61-92599.

Further, in JP-A-58-108457, prostaglandins inclusive of liquid obtained by attaching a biological sample to opposite-phase distribution chromatography is solidified by drying, and is dissolved thereafter and is made to react with a fluorescence prelabel agent for carboxyl group, to thereby esterify prostaglandins. The sample thus prepared is poured into a passage of a liquid chromatograph, and constituents are separated and measured with a fluorescence detector.

In the above-described prior art constructions, JP-A-61-92599 only suggests the possibility of prelabel, and in the methods according to JP-A-61-88148 and JP-A-58-108457, the operation for preparing the sample to be poured into the passage of liquid chromatography takes a long time and automation thereof is difficult. Therefore, these methods are unfit for a routine work such as clinical inspection.

Further, in the method according to JP-A-60-143766, not only the labeling reaction is made while the sample flows in a reaction coil, but also processing of the sample is performed entirely in the passage, and the number of analyzed analytes is about two analytes per hour.

SUMMARY OF THE INVENTION

It is an object of the present invention to provide an analytical method and an instrument for analysis utilizing liquid chromatography in which a plurality of samples may be analyzed effectively even when labeling reaction of the sample is made.

It is another object of the present invention to provide an analytical method and an instrument for analysis in which processing capability sufficiently usable in a routine work such as clinical inspection is obtainable.

The fact that the number of analyzed analytes per hour is few in the prior art proposal is caused by adopting a system in which a succeeding sample is poured after the whole process of analytical operations from pouring of the sample to detection with separation is complete.

In order to achieve above-described objects, according to the present invention, while an impurity eliminating column or a concentration column is processing a labeled specific sample, separated constituents of a sample which has proceeded the specific sample in a separation column and labeling reaction of a sample succeeding to the above-mentioned specific sample is made in a reaction processing portion.

When the present invention is described from another point of view, an entire analytical operation from preparing of a sample to detection with separation is divided into three process sections, a sample and a reagent are mixed to thereby prepare the sample in a first process section, the prepared sample is trapped in an impurity eliminating column or pre-column in a second process section, the sample sent from above-mentioned impurity eliminating column is separated into constituents and separated constituents are detected by a detector in a third process section, with the first, second and third process sections being set forward in parallel and, at the same time, operations proceed from the first process section to the third process section one after another.

In a biological sample containing a material such as a class of catecholamines and prostaglandins in which a plurality of constituents having a similar physical property are coexistent, it is effective to measure individual constituent by separation with chromatography. For example, in a class of catecholamines, epinephrine, norepinephrine and dopamine, etc. are coexistent, and in prostaglandins, thrombokisantin $B_2$, prostaglandins $E_2$, 6-ketoprostaglandins $F_{14}$ and prostaglandins $E_1$, etc. are coexistent. Therefore, it becomes possible to obtain individual constituent concentration by separating them by chromatography.

However, it is difficult to detect a class of catecholamines and prostaglandins under the state as is. Accordingly, in the present invention, a labeling agent is made to react a sample so as to label (form into a derivative) before constituent separation with a chromatography separation column, impurities such as impurities and excessive reaction reagents are removed with the precolumn thereafter so that detection accuracy is not reduced, and then, constituents of the sample formed into a derivative are separated by introducing a separation column, and an effluent from the separation column is detected with a detector. For example, when a fluorescence label agent is used for derivation, a fluorescence detector is used as a detector, and the property obtained by constituent to be inspected through derivation is utilized for detection. The detector is selected out of variety of equipment such as an absorption meter and a conductivity detector depending on labeling configurations.

In this method, respective samples are subject to a series of processings such as mixture with derivation reagent, proceeding of derivation reaction, transfer to the precolumn, constituent separation and detection. It is difficult for these series of processings to reduce the time within ten minutes under present circumstances even if a variety of devices are applied. Accordingly, if the analysis operation for a succeeding sample is started after the entire analytical operations on a proceeding sample is complete, it is impossible to perform measurement exceeding six analytes per hour.

Accordingly, in the present invention, the entire analysis operations from preparing to detection with separation of a sample are divided into three process sections so as to process the sample in respective process sections, to thereby obtain a higher efficiency. That is, in the second process section which is an intermediate process section, a processing of a trapped specific sample which has been already formed into a derivative is performed in the precolumn, and in the third process section, constituent separation processing and detection are performed for samples proceeding above-mentioned specific sample, and in the first process section, derivation reaction processing is performed for the sample succeeding to above-mentioned specific sample.

With this, it has become possible to analyze ten analytes or more in an hour, thus making it possible to apply such processing to a routine operations such as clinical inspection.

The boundaries between these process sections are not necessarily uniform, but may be varied to some extent depending on reaction conditions of derivation and constituent separation conditions.

In a preferred embodiment of the present invention, the start of derivation reaction of the sample is made in a preparing unit disposed outside the passage system. Here, sample processing is executed in a vessel. That is, mixing of a sample and a derivation reagent is performed in the vessel. Therefore, derivation reaction of the sample proceeds with no liquid flow or in a state wherein the sample is not diffused. When the reaction in the vessel is insufficient, or due to time restraints it is possible, after the sample and the reagent are mixed in the vessel, to introduce the mixed liquid sample into a metering conduit and also to continue the reaction there, but the derivation reaction proceeds in a chamber maintained in a state that the sample is not diffused.

Mixing of the sample and the reagent is not necessarily accompanied by stirring action, but it is only required that the sample and the reagent are added in the vessel so as to be coexistent. The partial pouring operation from a sample containing vessel to a reaction vessel or a mixing vessel in the preparing device and the partial pouring operation from the reagent containing vessel to above-mentioned reaction vessel or mixing vessel may be achieved by action of a movable pipetting nozzle. For simplifying the mechanism, it is desirable that just one pipetting nozzle is provided.

In a preferred embodiment of the present invention, the precolumn is disposed upstream of the separation column. Liquid for transferring the sample and washing of the precolumn is supplied to this precolumn through a passage change-over valve. The precolumn is called an impurity eliminating column or a concentration column. With the sample introduced into the precolumn, an impurity such as impurity and excessive reagent which is a primary factor of lowering measurement accuracy is discharged out of the precolumn by the supply of transfer and washing liquid, and the matter to be inspected is trapped. When this function is perceived, the precolumn is called an impurity eliminating column.

To the precolumn, a sample having a larger capacity than the sample containing capacity thereof is usually supplied. The supplied sample quantity is determined by a metering conduit having a predetermined volume. When the sample applied with reaction processing is introduced into the precolumn by the transfer and washing liquid, the matter to be inspected is trapped in the precolumn, and accumulated while the sample is flowing therein. When an eluent is supplied to the precolumn thereafter, the matter to be inspected, which is trapped in the precolumn, is desorbed and transferred toward the separation column. Since the volume of the sample liquid, when desorbed from the precolumn, is less than the sample volume introduced into the precolumn, it means that the sample introduced into the separation column has been concentrated. When this function is perceived, the precolumn is called a concentration column.

In a preferred embodiment of the present invention, sample receiving operation into the second process section is repeated at given time intervals with the length of processing time in the second process section as the reference. The operations in the first process section and the third process section are correlated so as to proceed with sample processing (including sample receiving preparation) in parallel with the second process section.

As the result of having realized parallel processing of a plurality of samples as described above, it becomes possible to make the average analysis time per analyte within six minutes, thus increasing the number of analyzed analytes per unit time.

DESCRIPTION OF THE PREFERRED EMBODIMENTS

In a preferred embodiment of the present invention, a first process section is operated principally on an auto sampler. Here, processing required for derivation of a sample is applied. In a second process section, operations intended for impurity eliminating and sample concentration are performed with a precolumn disposed in a passage as the center. In a third process section, constituent separation and detection of a sample with a separation column are performed.

Among the foregoing, in the second process section, a round of the process is accomplished in such a manner that a valve is changed over and the sample poured into a metering conduit of a sample introducing valve is transported to the precolumn by transfer and washing liquid and concentration and impurity elimination are performed, and thereafter, a column change-over valve is changed over so as to dissociate the sample by eluent and transfer the same to the separation column, and the column change-over valve is changed over again so as to apply the prepared liquid to the precolumn, to thereby restore the precolumn to a state in which it is able to receive a succeeding sample.

The analytical operation is executed by having the operation in the first process section, for a sample on an auto sampler start at time intervals of one cycle in the second process section, and performing processings in the first, the second and the third process sections in parallel on a plurality of samples which are analyzed in succession. That is, when a first sample is moved to the operation in the second process section after completing the operation in the first process section, the operation in a first process section of a succeeding second sample is started, and, when the first sample is transferred to the operation of the third process section after completing the operation in the second process section, the succeeding second sample is transferred to the operation in the second process section and the operation in the first process section of the third sample is started.

As to the analytical processing time of the present instrument according to above-described analytical steps of procedure, the total time for the first through the third process sections is required for a first analyte, but analytical results are obtainable in one cycle of a program, that is, at required time intervals in the second process section for and after a second analyte, thus making it possible to remarkably reduce the analyte processing time in continuous analysis. It is not necessarily required to specify details of operation contents in respective process sections. However, since an analytical program is executed by means of a repetitive program with the required time of the second process section as one cycle, it is desirable to determine sections taking time distribution among respective process into consideration to generate a program so as to be suitable for execution of this program. It is also desirable that the required time of respective process sections is within the time of above-mentioned one cycle. In this case, analysis may proceed by performing parallel processing analyte by analyte for every process section. However, there is a possibility that derivation reaction takes a longer time than the time of above-mentioned one cycle because derivation reaction takes a long time depending upon analytical objects and so forth. This time difference may be compensated by a method of providing a plurality of reaction places and so on. For example, if the time difference is twice as long as the cycle, it is possible to process analyte by analyte in every cycle.

It is a requirement of the third cycle that the time required from a separated constituent passes through a detector until the measurement thereof is completed is within the time of above-mentioned one cycle, and electrical processing such as arithmetic indication of data need not necessarily be included in one cycle.

1.2-diphenylethylenediamin (DPE) may be used for example, for a fluorescence label agent as a derivation reagent of a class of catecholamines, and prepared fluorescence label agent solution contains DPE at 60 mM, potassium ferricyanide at 2 mM, acetonitrile at 40% and so forth. Further, a liquid containing acetonitrile, methanol and aqueous solution at the ratio of 5:2:4 is used for instance for eluent supplied to the separation column for separating a class of catecholamines. In this case, lithium nitrate at 50 mM and dodecyl sodium sulfate at 10 mM are contained in the aqueous solution.

Monodancyl cadaverine (MDC) may be used for fluorescence label agent as a derivation reagent of prostaglandins. The prepared fluorescence label agent solution contains MDC at 6 mM, diethyl phosphorocyanitate (DEPC) and so forth. Further, a liquid of a system composed of water, tetrahydrofuran and acetnitrile may be used for the eluent for separating prostaglandins. It is desirable that an excitation wavelength of a fluorescence detector is at 340 nm and a fluorescence wavelength is at 520 nm.

The present invention is applicable when a single separation column is used. In this case, only a simple structure is needed as compared with a case in which a plurality of pieces of separation columns are used. Biological samples to which the present invention is applicable preferably are blood plasma, blood serum, urine and so forth.

An example of a catecholamine automatic analyzer to which the present invention is applied will be explained hereafter with reference to the accompanying drawings.

DETAILED DESCRIPTION

Figure 1:
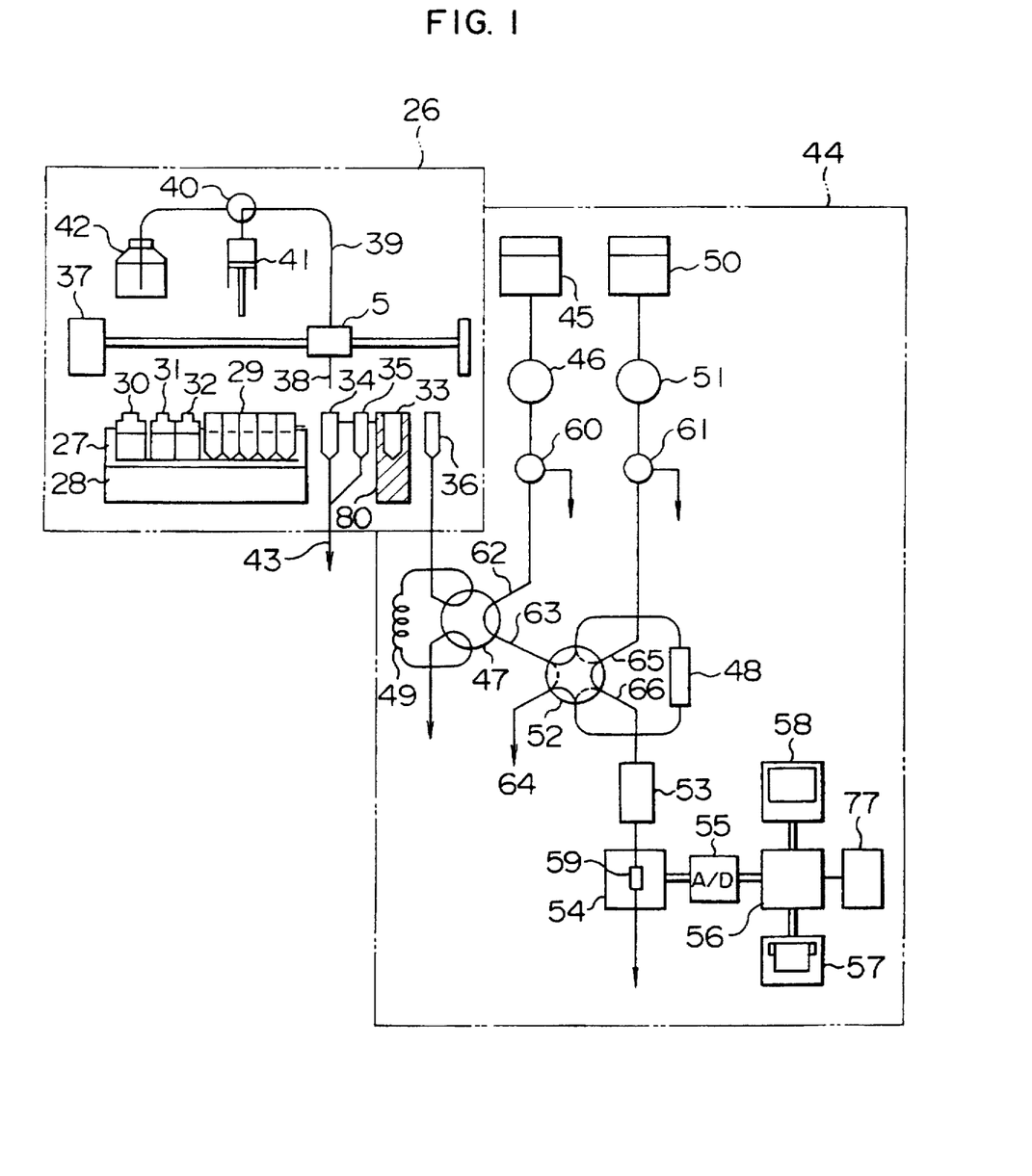
FIG. 1 is a schematic view of a general composition of an embodiment of the present invention.

As shown in FIG. 1 a catecholamine automatic analyzer includes a preparing portion 26 provided with various vessels and a partial pouring mechanism and a concentrating and separating portion 44 which performs concentrating operation and separating operation of a sample in a passage. Hereafter, the preparing portion 26 is called an auto sampler for convenience's sake, and the concentrating and separating portion 44 is called an analytical portion.

A sample rack 27 is charged on a sample stage 28 of the auto sampler 26. The sample rack 27 holds a plurality of sample vessels containing blood plasma samples. Further, on the sample rack 27, a reaction reagent vessel 30 for fluorescence labeling, an internal reference liquid vessel 31 and a reference sample vessel 32 are disposed. The reaction vessel 33, a nozzle washing tank 34, a drain port 35 and an injection port 36 are provided at fixed positions near to the sample stage 28.

A partial pouring nozzle 38 acts to partially pour a sample and a reagent into the reaction vessel 33 by pipetting and to transfuse samples which have reacted from the reaction vessel 33 to the injection port 36. A drive mechanism has a drive function in XYZ directions and is able to drive the partial pouring nozzle 38 lengthwise and crosswise and up and down freely so as to move it to positions of vessels and ports on the sampler. The upper end of the partial pouring nozzle 38 is connected to a partial pouring pump 41 and a washing liquid tank 42 by a fine tube 39 such as a plastic tube through a three way valve 40. The partial pouring pump 41 employs a syringe pump which is driven by a pulse motor. A constant temperature block 80 is provided for the purpose of maintaining the temperature of the reaction vessel 33 at a predetermined temperature. Also, a cooling unit is incorporated on the sample stage 28 so as to keep samples and reagents on the sample rack 27 at a low temperature during analysis.

The analytical portion 44 includes a precolumn passage system which performs concentration of samples and impurity eliminating, a separation column passage system which performs separation of sample constituents and a measurement and arithmetic portion. In the precolumn passage system, transfer and washing liquid of a liquid tank 45 is fed at a constant flow velocity by a pump 46, and flows to a precolumn 48 through a sample introducing valve 47. At the sample introducing valve 47, a metering conduit 49 for measuring a predetermined quantity of sample liquid poured from the pouring port 36 of the auto sampler is provided.

In the separation column passage system, eluent in an eluent tank 50 is charged at a constant flow velocity by a pump 51, and flows into a single separation column 53 through a column change-over valve 52. By changing over the column change-over valve 52, the eluent flows through a precolumn 48 and transfers the sample processed in the precolumn 48 to a separation column 53. A measurement and arithmetic portion consists of a fluorophotometer 54 for measuring fluorescence intensity of sample constituents which is effluent from the separation column 53, an A/D conversion portion 55 for performing arithmetic processing and display of measurement results, a control portion 56, a printer 57, a CRT 58 and so forth, and the fluorophotometer 54 is provided with a flow cell 59. Change-over valves 60 and 61 are provided so that liquid in pumps 46 and 51 may be purged as need.

The analysis according to the present embodiment is performed in the following sequence:

(1) Fluorescence labeling operation of a sample on an auto-sampler;
(2) Concentration and impurity elimination operations by a precolumn; and
(3) Separation and measurement of sample constituents by a separation column.

Figure 2:
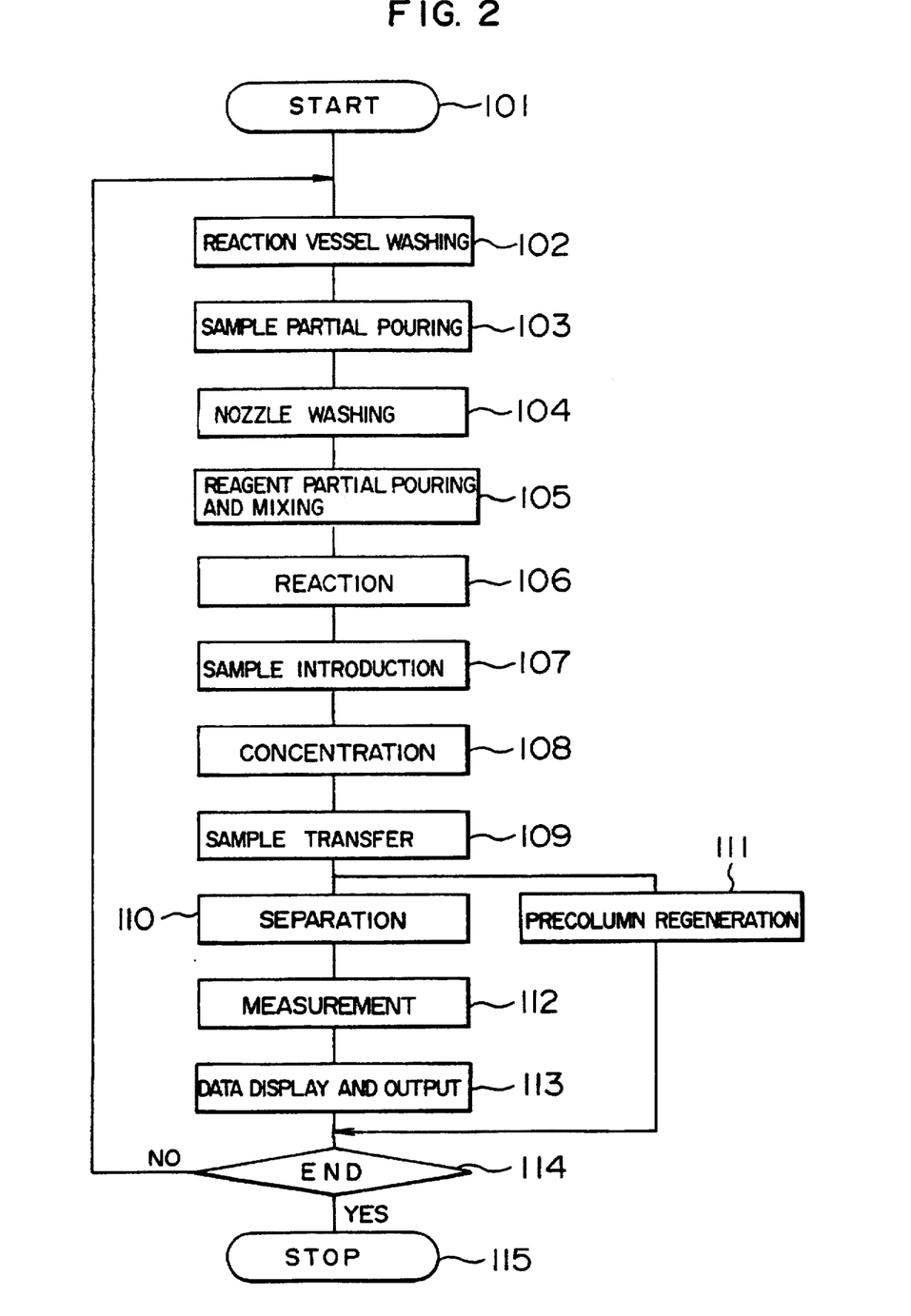
FIG. 2 is a flow chart depicting the analytical operation in the embodiment of FIG. 1.

Referring to the flow chart of FIG. 2, after starting an analytical operation in a step 101, the reaction vessel 33 is washed in a step 102. At this time, the nozzle 38 is moved to the position of the reaction vessel 33, and washing liquid from a washing liquid tank 42 is poured into the reaction vessel by actuating the pump 41. A larger volume of the washing liquid than the volume of the reaction vessel 33 is poured, and excessive washing liquid overflows so as to drain toward a discharge tube 43 through a drain port 35. Then, the nozzle 38 is lowered to the bottom of the reaction vessel 33 so as to suction the washing liquid in the reaction vessel 33, and the nozzle 38 is moved to the drain port 35 so as to discharge suctioned liquid. Prior to this operation, it is required to suction some air at the point of the nozzle 38 in advance so that suction contaminated washing liquid may not be diffused in fresh washing liquid in the nozzle. (The operation of suctioning air bubbles so as to produce a boundary prior to suction is required in case of suctioning samples and following reagents.) Washing of the reaction vessel 33 is completed by repeating the above-described operations a plurality of times (for example, three times).

In a step 103, partial pouring of a sample into the reaction vessel 33 is performed. The nozzle 38 is moved to the position of the internal reference liquid vessel 31 and is lowered so as to suctioned a predetermined quantity of the liquid, and then, the nozzle 38 is moved to the position of a sample vessel 29 to be analyzed so as to suctioned a predetermined quantity of sample. Thereafter, the nozzle 38 is moved to the position of the reaction vessel 33 so as to partially pour the sample and the internal reference liquid which have been suctioned and in the nozzle 38 into the reaction vessel 33. The internal reference liquid is a reference liquid used for correcting variation of recovery of the column and so forth. An isoproterenol is used as a reference material in the present embodiment.

In a step 104, the nozzle 38 is washed. In this case, the nozzle 38 is moved to the drain port 35, the washing liquid is discharged and the internal reference liquid and stain on the inner wall of the nozzle due to the sample are washed away. Thereafter, the nozzle is moved to the washing tank 34 and lowered into the tank, and the washing liquid is discharged thereby to wash the outside of the point of the nozzle 38.

In a step 105, a reagent is added to the reaction vessel 33. The nozzle 38 is moved to a position of a vessel 30 of a reaction reagent, a predetermined quantity of derivation reagent is suctioned into the nozzle and poured into the reaction vessel 33 so as to be mixed with the sample and the internal reference liquid which have been previously poured therein. Other than the above, mixing may be made by a method in which air is suctioned into the nozzle in advance and the nozzle is inserted into the vessel so as to discharge air, a method of vibrating the vessel mechanically or electrically from the outside and so forth. However, if the liquid is easily mixed and the discharge quantity is comparatively large, mixing is possible sometimes only by discharging at a high velocity.

In a step 106, fluorescence labeling reaction is started so that derivation to a fluorescent material for a class of catecholamines is performed. The mixed liquid of a sample and a derivation reagent (hereafter referred to as sample liquid) in the reaction vessel 33 is left as it is for a predetermined time in the reaction vessel 33 which is heat insulated at a constant temperature so as to proceed with reaction, to thereby perform fluorescence labeling.

In a step 107, reaction liquid in the reaction vessel 33 is introduced into a metering conduit 49. The sample liquid formed into a derivative which has essentially completed a reaction in the reaction vessel 33 is suctioned into the nozzle 38, the nozzle is moved to the pouring point 36 and inserted therein, and the sample liquid is poured into the metering conduit 49 with the sample introducing valve 47 being disposed in the state shown in FIG. 1. When the sample introducing valve 47 is changed over after the metering conduit 49 is filled with sample liquid, the metering conduit 49, connected to the port of the change-over valve 52, is connected between a passage 62 and a passage 63, and a predetermined quantity of sample liquid is transferred to the precolumn 48 by the flow of transfer and washing liquid.

Concentration

In a step 108, catecholamines in the precolumn 48, impurity and excessive reagent are are eliminated, and concentration of the sample liquid is conducted at the same time. When the sample liquid is introduced into the precolumn 48 by the flow of transfer and washing liquid, the sample is trapped by adsorption and accumulated in the precolumn 48. At this time, impurity and excessive reagent which are impurities disturbing the measurement pass through the precolumn and are discharged through a discharge port 64.

In a step 109, the sample which is trapped with impurity removed is desorbed from the precolumn 48 and introduced to the separation column 53. When a column change valve 52 is changed over from a state shown in solid line to a state shown in broken line in FIG. 1, the precolumn 48 is connected between passages 65 and 66, the eluent flows through the precolumn 48, and the sample concentrated in the precolumn 48 is dissociated and sent to the separation column 53, thus starting separation. When the column change-over valve 52 is changed over again at a point when entire samples are moved to a passage 66 (solid line state shown in the FIG.), the eluent flows directly to the separation column 53 without going through the precolumn 48, and transfer and washing liquid starts to flow in the precolumn 48.

In step 110, the eluate continues to flow into the separation column 53, and constituent separation of a class of catecholamines is performed. Norepinephrine (NE), epinephrine (E) and dopamine (DA) form a constituent band, which is effluent from the separation column.

In parallel with separation of sample constituents in the step 110, in a step 111, transfer and washing liquid is applied to the precolumn 48, thereby to restore it to a state under which a succeeding sample may be received.

In a step 112, eluent from the separation column 53 is observed with the fluorophotometer 54. The sample constituents which have been separated by and effluent from the separation column 53 successively flow in the flow cell 59 of the fluorophotometer 54, and fluorescence intensities of respective separated constituents are detected and concentrations of respective constituents are obtained through arithmetic processing.

In a step 113, data obtained in the step 112 are outputted and displayed by a printer 57, a CRT 58 and the like. In a step 114, it is determined whether all the samples on the auto sampler 26 have been processed or not. If some are remaining, the process is returned to the step 102, and if all have been processed, the process proceeds to a step 115, thus completing analytical operation of the instrument.

Figure 3A:
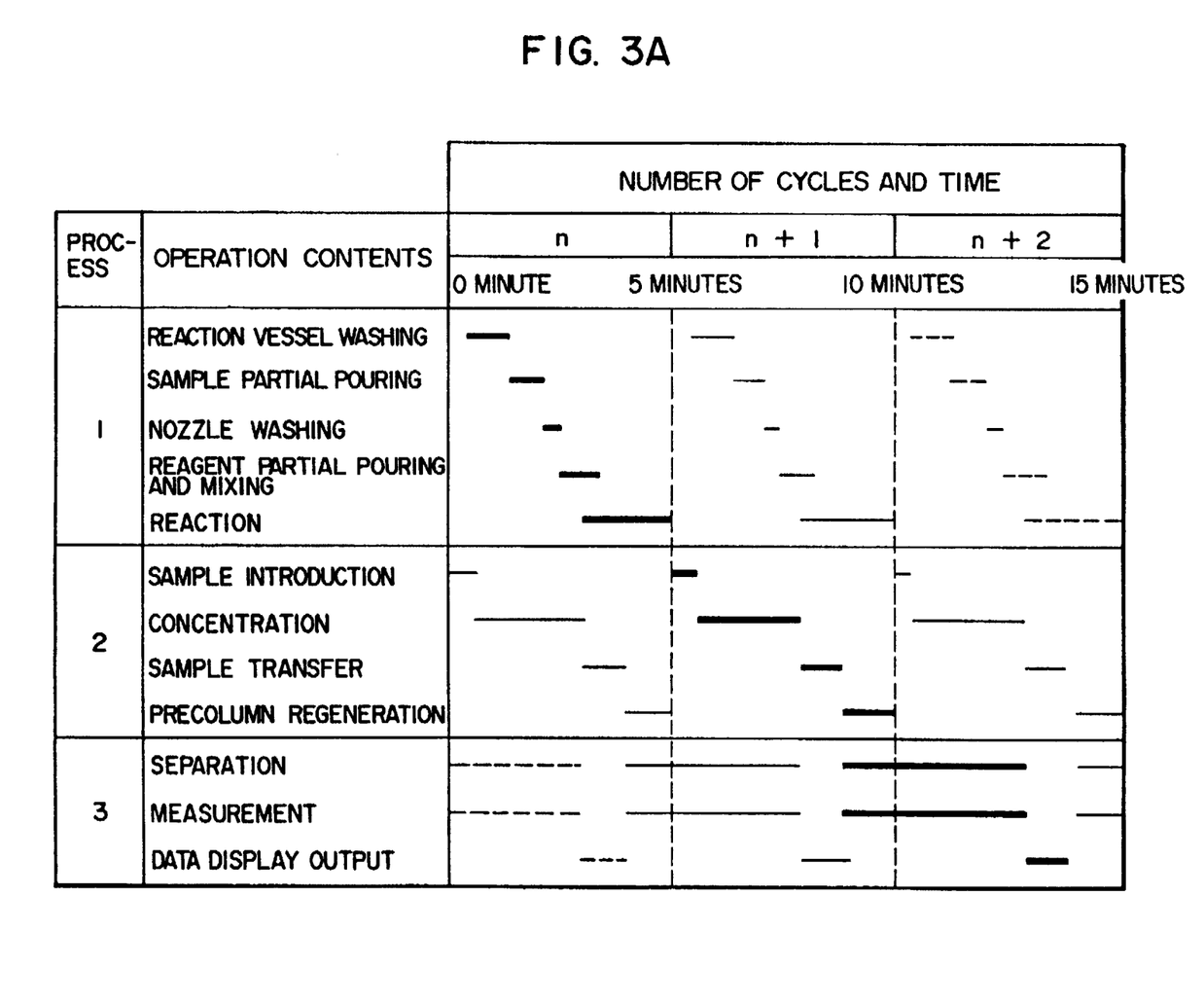
FIGS. 3A and 3B are charts of an example operation program depicting operation timing of respective parts in the embodiment of FIG. 1.
Figure 3B:
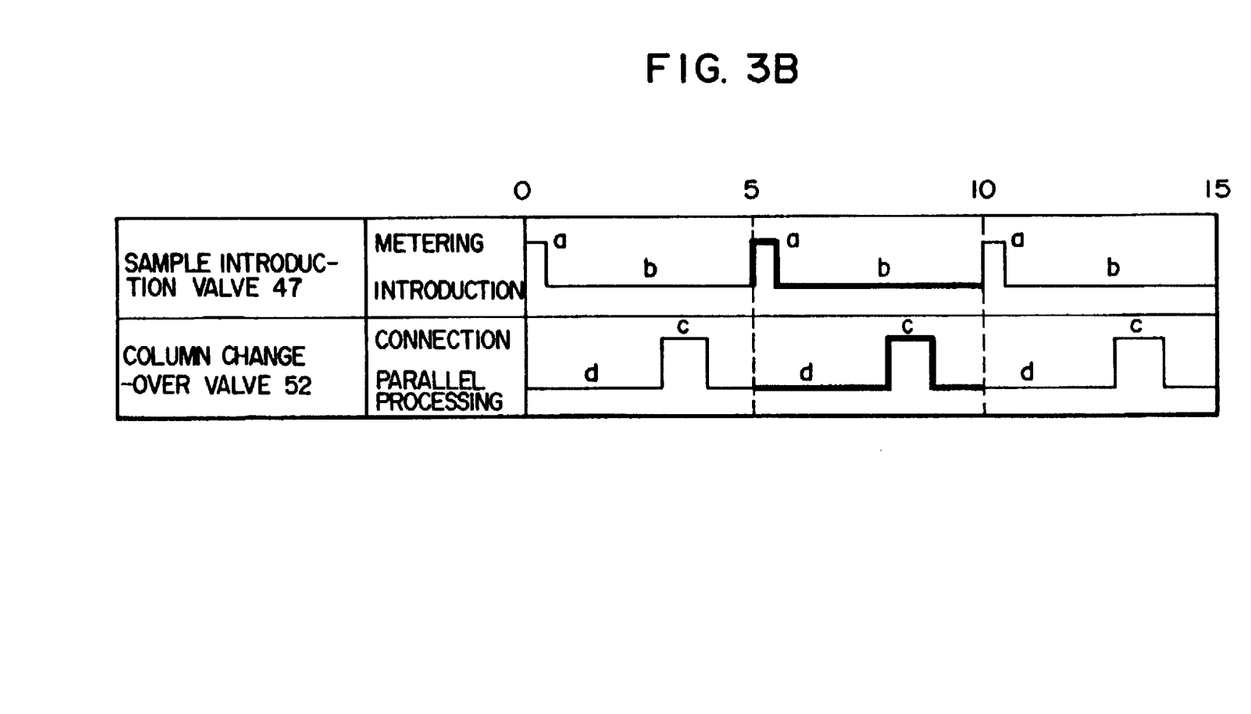

Analytical steps of procedure on one analyte have been described above, but steps of procedure of continuous processing of a plurality of analytes according to the present invention will be explained in succession. FIG. 3A and FIG. 3B show an example of an analytical program thereof.

An ordinate in FIG. 3A represents operation contents of the analytical flow chart described previously by sectioning into processes 1, 2 and 3. The first process shows principally the operation on the auto sampler for forming the sample into a derivative, the second process shows the operation of sample concentration by the precolumn and the third process shows the operation of separation and measurement of sample constituents by the separation column. Section boundaries between respective processes are formed so that appropriate time distribution among respective processes is obtainable in point of a program. An abscissa of FIG. 3A represents a cycle number and elapsed time of a progressing analytical program. The program is made so that operations in first, second and third processes are completed in one cycle, respectively.

FIG. 3A shows a state of analyzing an nth analyte as the center. Solid thick lines show the state. Solid fine lines show states of an (n+1)th analyte and an (n−1)th analyte, and chain lines shows states of an (n−2)th analyte and an (n+2)th analyte. FIG. 3B shows the action of a change-over valve. A "metering" state a of the sample introducing valve 47 shows a state that sample liquid may be poured from the pouring port 36 into the metering conduit 49, that is, the state shown in FIG. 1, and a "introduction" state b shows a state in which the valve is changed over and the metering conduit 49 is connected to a precolumn passage. Further, a "connection" state c of the column change-over valve 52 shows a state in which the precolumn 48 is connected to a separation column passage, and a "parallel processing" state d shows a state in which separation is made and transfer and washing liquid is flowing, that is, the state shown with solid lines in FIG. 1. Respective change-over valves operate repeatedly in every cycle.

The analytical operation proceeds by starting analysis of a first analyte (an analyte analyzed in the first place) in a first cycle, and starting analysis of samples on the auto sampler in succession cycle by cycle. FIG. 3A shows operation states from an nth cycle to an (n+2)th cycle. That is, analysis of an nth analyte (an analyte analyzed in the nth place) is started in the nth cycle, and the operation in the first process is performed. The operation of the second process of an (n−1)th analyte in which analysis has been started previously in parallel with the above and the operation of the third process of an (n−2)th analyte are proceeding. Then, in an (n+1)th cycle, the nth analyte proceeds to the operation of the second process, and the operation of the first process of a succeeding (n+1)th analyte is started. In parallel with this, the operation of the third process of the (n−1)th analyte is being performed. Furthermore, in an (n+2)th cycle, the operation of the third process of the nth analyte and the operation of the second process of the (n+1)th analyte are performed, and the operation of the first process of a succeeding (n+2)th analyte is started.

According to analytical steps described above, the analytical processing time of the present instrument requires the total time of the first, the second and the third processes, that is, the time for three cycles, when only one analyte is analyzed, but it is possible to analyze analytes one by one in every cycle when a plurality of analytes are analyzed successively. Since the time required for one cycle is five minutes in the present embodiment, the processing time per analyte is five minutes.

Since it is desirable to provide processing capacity of ten analytes or more per hour in chromatography of a class of catecholamines, the time for one cycle is required to be within six minutes.

Figure 4:
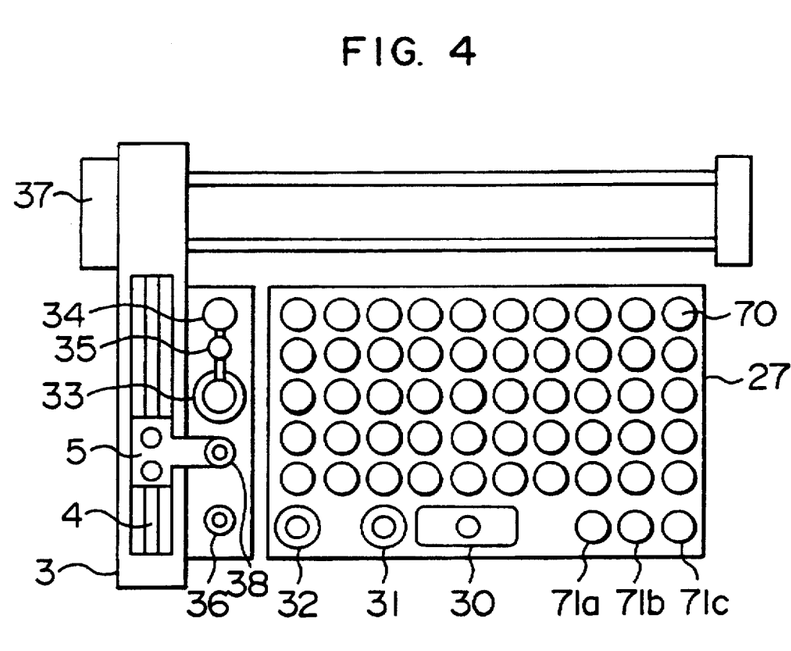
FIG. 4 is a plane view of an auto sampler of FIG. 1.

The auto sampler 26, as shown in FIG. 4, includes a detachable sample rack 27 on the sample stage 28, sample vessel inserting ports 70 and sample vessels containing samples to be analyzed are charged and arranged thereon. The inserting ports 70 are arranged in a matrix of fifty positions with a row of ten ports 70 an a column of five insert ports 70. On the sample rack 27, there is a place for the reaction reagent 30, the internal reference liquid 31 and the reference sample 32, and furthermore, urgent analyte vessel insertion ports 71a, 71b and 71c are provided so that urgent interrupt measurement may be made during analysis. Further, the reaction vessel 33, the nozzle washing tank 34, the drain port 35 and the pouring port 36 to the metering conduit 49 are provided at fixed positions on the side of the sample rack 27, respectively. The partial pouring nozzle 38 is held by a holding portion 5 which is slidable on a shaft 4 of a movable body 3, driven longitudinally, transversely and up and down in X, Y and Z directions freely by a drive mechanism 37 and positioned any time at positions of above-described respective vessels or ports, thus performing required operations.

The analytical operation is started by installing the sample rack 27 on which samples to be analyzed and reagents are arranged on the sample stage 28 of the auto sampler 26 and pressing an analysis start switch of a control panel 77.

Figure 5A:
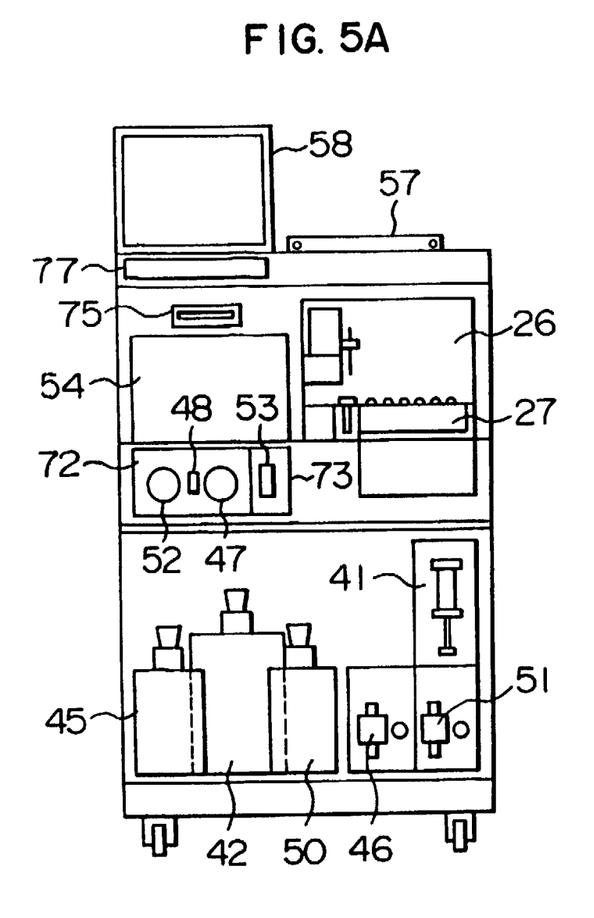
FIG. 5A is an exterior view of the instrument shown in FIG. 1.
Figure 5B:
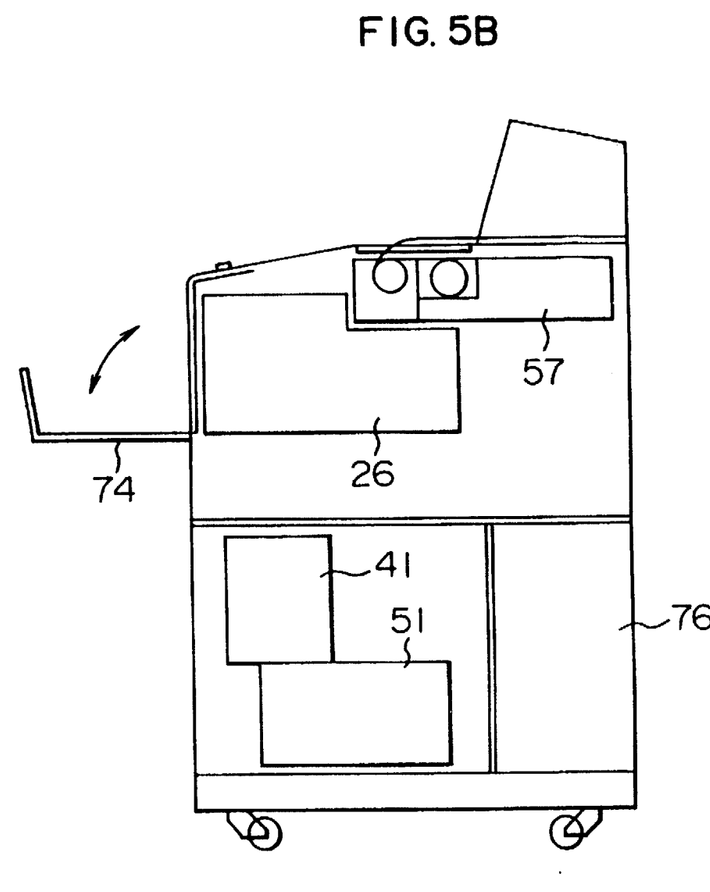
FIG. 5B is a side view of the instrument shown in FIG. 5A.

FIG. 5A and FIG. 5B are composition layout drawings showing an instrument of the present embodiment. The instrument is of a vertical type and has a composition in which all of respective units required for analysis are incorporated.

The instrument is partitioned into two stages, and the auto sampler 26, the fluorophotometer 54 and a column panel 72 are disposed on the upper stage, and the precolumn 48, the separation column 53, the sample introducing valve 47 and the column change-over valve 52 are disposed on the column panel 72. The temperature of the separation column 53 is controlled with a constant temperature block 73 in order to maintain a constant temperature state during analysis. Installation and removal of the sample rack 27 on and from the auto sampler 26 are performed by opening and closing a cover 74. A floppy disc 75 for storing measurement data is incorporated above the fluorophotometer 54.

On the lower stage of the instrument, the washing liquid tank 42, the transfer and washing liquid tank 45, the eluent tank 50, the partial pouring pump 41, the pump 46 for feeding transfer and washing liquid and the pump 51 for feeding the eluent are arranged, and the liquid required for an analytical unit on the upper stage of the instrument is fed therefrom. Besides, an electrical system 76 such as a power source, substrates and the like are housed in a rear part on the lower stage of the instrument. The printer 57, the CRT 58 and the control panel 77 for performing input operation for analysis by the present instrument are disposed on an upper face of the instrument.

Figure 6:
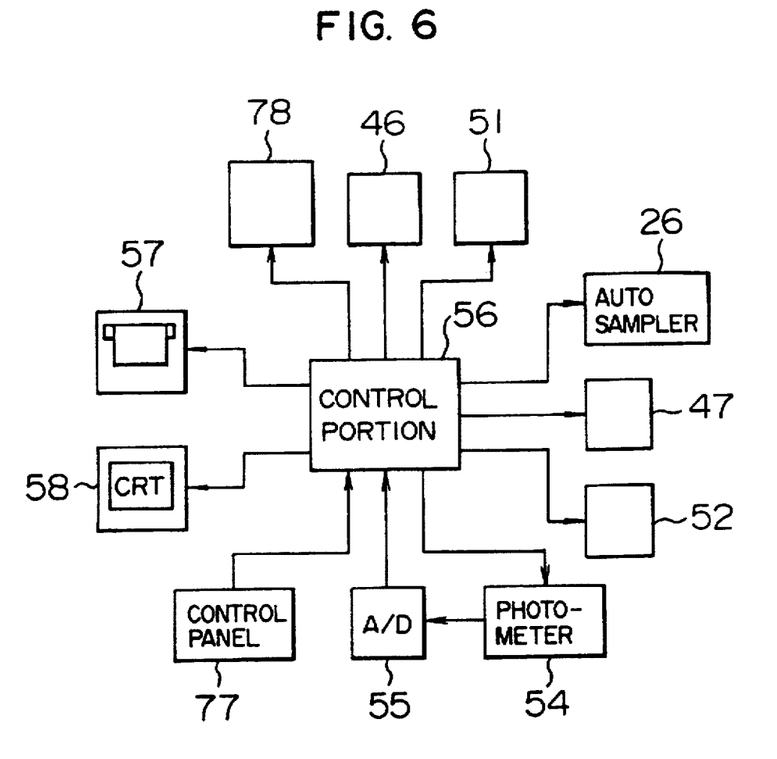
FIG. 6 is a control system diagram of the instrument shown in FIG. 1.

FIG. 6 shows a control system diagram of the present embodiment. Analytical control by the instrument in the present embodiment described above is performed with a control portion 56 as a center the input from the control panel 77. First, when a power switch is put ON, a temperature control unit 78 is actuated, and a light source of the fluorophotometer 54 is lit up at the same time. Next, when a switch for analysis preparation is put ON, the pump 46 and the pump 51 start to feed the liquid. When an analysis start switch is put ON after installing the sample rack 27 on the auto sampler 26, the auto sampler 26, the sample introducing valve 47 and the column change-over valve 52 start the operation, and analytical operation is performed in accordance with analytical steps explained with reference to FIG. 2 and FIG. 3. Measurement results are printed by the printer 57 and also displayed on the CRT 58 after data processing of signals from the fluorophotometer 54 in the control portion 56 through an A/D converter 55.

Figure 7:
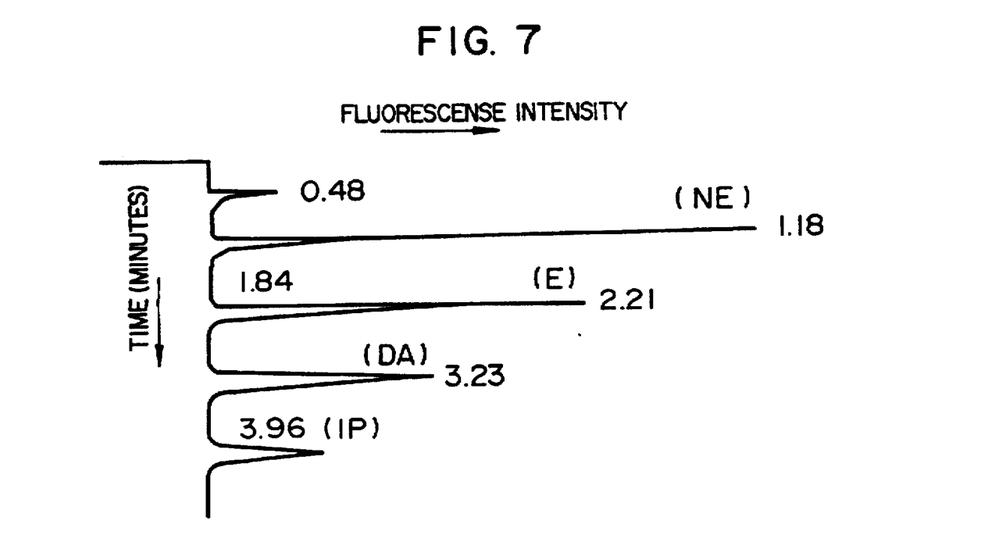
FIG. 7 is a graphical illustration of analytical results of a class of catecholamines.

FIG. 7 shows an example of analysis results of a class of catecholamines with the instrument of the present embodiment. Numeric values indicated at respective peaks show the retention time, that is, from start of separation until respective separated constituents reach a detector. In the present instrument, start of separation is made from the time when the column change-over valve 52 is changed over and the sample concentrated in the precolumn 48 is started to be transferred to the separation column 53, and the first peak at 0.48 seconds shows a peak detected because the transfer liquid filled in the precolumn passes the detector in advance of the sample which is separated and effluent. Then, sample constituents separated by the separation column 53 are effluent in a sequence of norepinephrine (NE), epinephrine (E) and dopamine (DA), and isoproterenol of an internal reference material which was added as an internal reference material is finally effluent and detected. Concentrations of respective constituents are obtainable from respective peak areas.

In the case of the present analysis example, the objective separation has been terminated in a little over four minutes after start of separation, that is, after the column change-over valve 52 is changed over. That is, separation within ⅓ cycle which was explained previously is possible in accordance with this analysis example.

In the present instrument, outputs when used in a routine work are shown by printing an analyte number and marks and concentrations of analyzed three constituents on the printer 57, and CRT display and printer output of a chromatogram such as shown in FIG. 7 are made possible at need. Further, only one piece of precolumn is adopted in the present embodiment, but a plurality of columns are sometimes used. For example, there is a method in which two pieces are used in series so as to divide the work of elimination of water soluble impurity and elimination of hydrophobic impurity and so forth.

Figure 8:
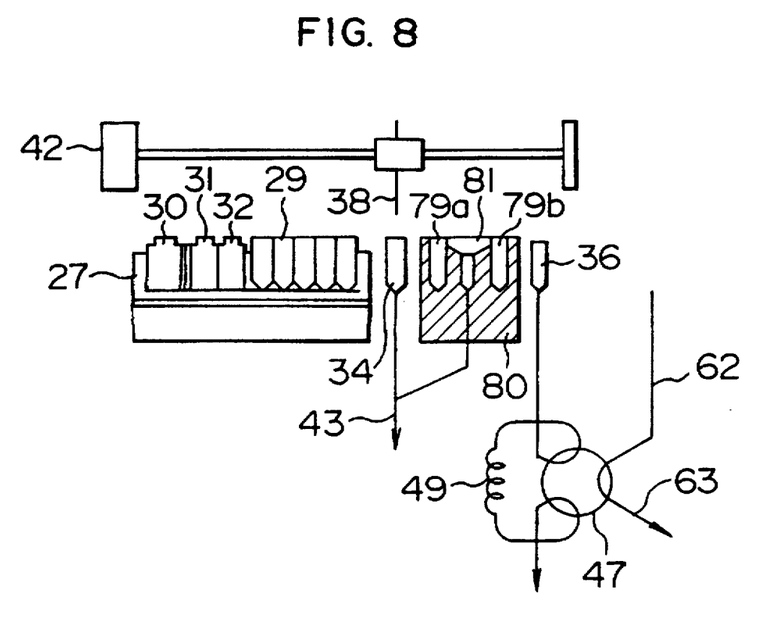
FIG. 8 is a schematic block diagram of a portion of a modified embodiment of the present invention.

A first modified example shown in FIG. 8 shows a method in which two reaction vessels are provided. That is, it is structured so that two reaction vessels 79a and 79b are provided on the auto sampler, with each vessel being heat insulated with a constant temperature block 80, and washing liquid which overflows in washing flows to a drain port 81. This system is used when the operation of derivation on the auto sampler, that is, when the first process takes a longer time than the time of one cycle because of such reason that reaction takes time. That is, it is possible to complete the processing of one analyte each in every cycle by partially pouring a sample and a reagent alternately into two reaction vessels at time intervals of one cycle so as to proceed with reaction. If the operation time takes twice or more of one cycle, however, it is necessary to increase the number of reaction vessels.

Figure 9:
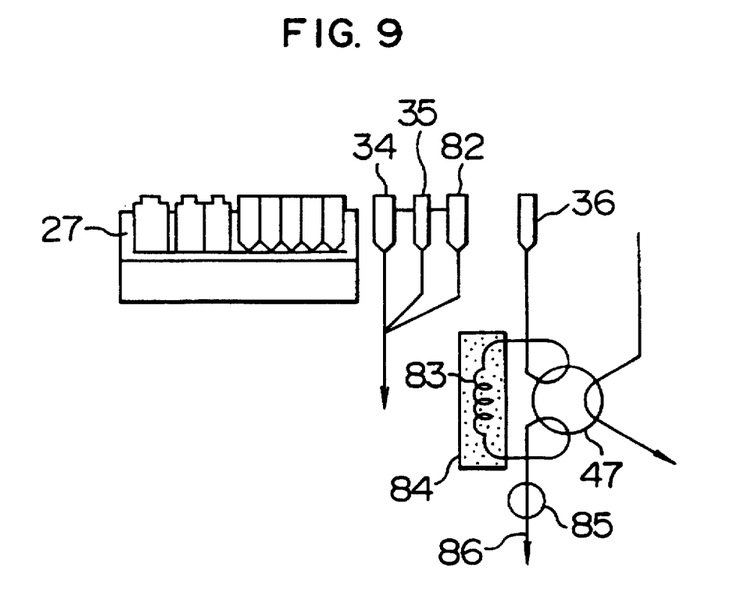
FIG. 9 is a schematic block diagram of a portion of a further modified embodiment in accordance with the present invention.

A second modified example shown in FIG. 9 is an example in which reaction proceeds in a metering conduit of a sample introducing valve. A vessel 82 on the auto sampler is used as a mixing vessel which mixes a sample with a reagent, and the reaction liquid which has been started to react by mixing is poured into a metering conduit 83 from the pouring port 36 using the partial pouring nozzle 38, where the liquid is left, e.g. temporarily stored, as it is for a certain time under a state that the liquid is not circulated so as to show reaction. In this case, the metering conduit 83 is maintained at a predetermined constant temperature by a constant temperature block 84, and a stop valve 85 is provided in an outlet passage so that the liquid is not moved during reaction. This system cannot be adopted for a reaction for a long time because the reaction time is determined by operation interval of the sample introducing valve 47. However, since the metering conduit 83 is formed by winding a synthetic resin tube and the like in a coil form, temperature control is easy and degree of freedom is provided with respect to location. Thus, there is such an advantage that, for example, the system may be formed in one body with a constant temperature block of the separation column.

Figure 10A:
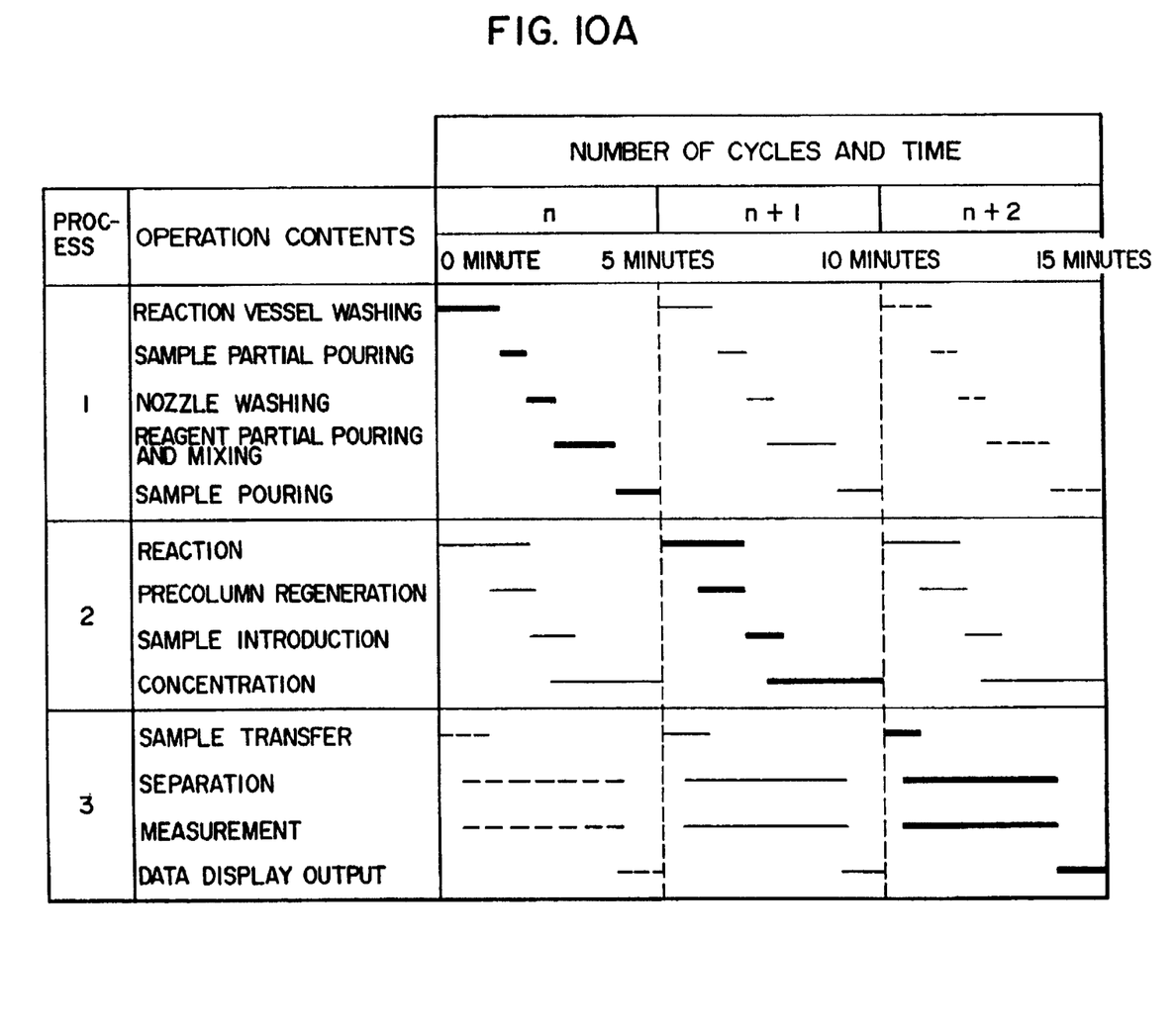
FIGS. 10A and 10B provide an example of an operation program depicting operation timing of respective portions of the instrument of FIG. 9.
Figure 10B:
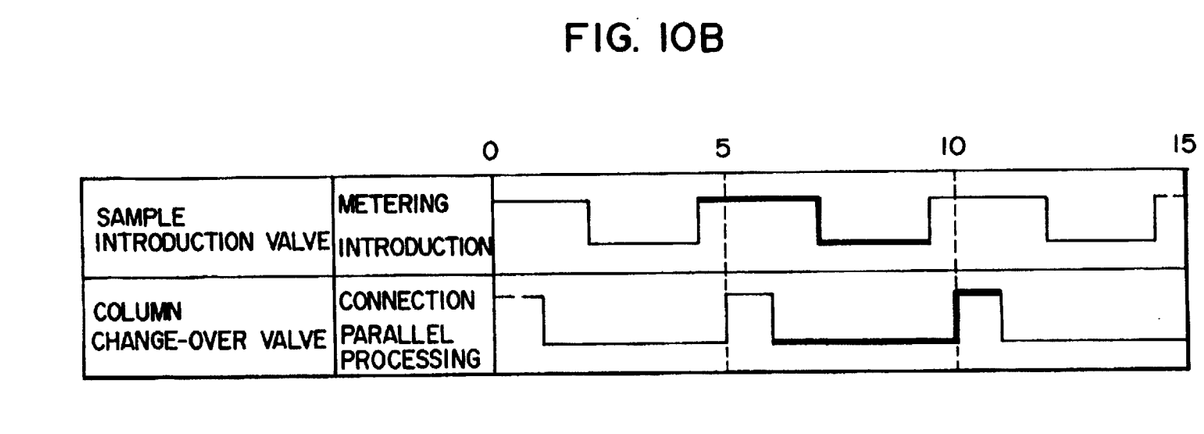

FIG. 10A and FIG. 10B show a program example in the second modified example shown in FIG. 9. It is the same as the program shown in FIG. 3 in the above-described embodiment in that the process is divided roughly into a process 1 showing operation on the auto sampler for derivation, a process 2 showing concentrating operation by a precolumn and a process 3 showing operations of separation and measurement by a separation column, but boundaries between sections of respective processes are slightly different. That is, in the present program, a program is made such that a first process covers until sample liquid is poured into the metering conduit 83 of the sample introducing valve 47, a second process covers from start of reaction in the metering conduit where the sample liquid is temporarily stored for the reaction time interval depicted in FIG. 10A and the second process terminates with concentration of the sample by the precolumn, and a third process starts from transfer of the sample to the separation column. In such a manner, the analytical operations may be divided roughly into operations of auto sampler, precolumn and separation column and respective operations may be performed continuously on analytes to be analyzed by a repetitive program in the examples shown in FIG. 9 and FIG. 10, too.

Either of above-described modified examples shows that reaction places are fixedly provided, but there is also a method in which nonreturnable vessels are used as an example other than the above. That is, in this method, reaction vessels in the same number as the number of samples are arranged on the auto sampler, and reaction is made to generate using one piece of reaction vessel for each analyte. This method has such merits that it is not required to wash the reaction vessels one by one, and by pouring samples and reagents partially in succession into a plurality of vessels at time difference even at a place where reaction takes a long time, it is possible to feed sample liquid formed in a derivative to an analytical portion at time intervals of above-mentioned one cycle. However, since reaction vessels in the same number as the number of samples are required, there is a drawback that the auto sampler becomes large in size.

An example of an automatic analytical instrument of catecholamines has been described above as an embodiment of the present invention. However, the applicable scope of the present invention is not necessarily limited to the scope of this embodiment. That is, the present invention may be applied to analysis of various materials as analysis objects such as amino acid, bile acid and guanidine other than catecholamines. Further, the method of derivation and the employed detector are not necessarily limited to a fluorophotometric method, but also such a method that measurement is made by using an ultraviolet or visible photometer by enzyme activity or a UV activity method may be applied. Furthermore, various modified examples in a concrete method for performing derivation, that is, reaction places, steps of operation procedure and composition of program may be considered.

As described above, according to the present invention, such remarkable effects are obtainable that analytical processing time of an automatic analytical instrument applied with liquid chromatography which previously required a long time including derivation of samples and sample concentration processing by the precolumn may be reduced sharply, for example, the operation of a routine operations such as clinical inspection in a hospital may be automated.

What is claimed is:

1. An analytical instrument for analyzing a plurality of samples, the analytical instrument comprising:

an analytical section including, in a flow line, a metering conduit, a precolumn, a separation column and a detector;

a preparing section including, outside of said flow line, sample containers, a labeling reagent container, a mixing container, and delivering means including a pipette having a pipette nozzle, said delivering means delivering a sample from any of the sample containers to the mixing container, delivering a labeling reagent from the labeling reagent container to the mixing container and delivering a mixture of the sample and the reagent from the mixing container to the metering conduit of the analytical section in said flow line, each delivering operation being accomplished by actuating said pipette nozzle;

said analytical section further includes a first change-over valve in said flow line between said metering conduit and said precolumn for selectively connecting and disconnecting flow between said metering conduit and said precolumn, said first changeover valve being connected to a device for providing a carrier liquid to the precolumn through the first changeover valve and, when said first changeover valve is connecting said metering conduit and said precolumn, said carrier liquid being directed through the metering conduit for transferring the mixture in the metering conduit to the precolumn, and a second changeover valve in said flow line between said precolumn and said separation column for selectively connecting and disconnecting flow between said precolumn and said separation column, said second changeover valve being connected to a device for providing an eluent to the separation column through the second changeover valve and when said second changeover valve is connecting said precolumn and said separation column said eluent being directed through the precolumn in order to transfer labeled constituents of the sample which are withdrawn in the precolumn to the separation column;

said delivering means, after finishing a filling of said metering conduit with a mixture of a first sample and a labeling reagent from said mixing container, washing said mixing container and, delivering a second sample and labeling reagent to said mixing container with said pipette nozzle and washing said pipette nozzle before filling said metering conduit with the mixture of the second sample and labeling reagent; and wherein said instrument further comprises control means for controlling the first and second changeover valves and the delivering means so as to enable a mixing operation of a third sample and labeling reagent subsequent to the mixing of said second sample and labeling reagent in the preparing section, a withdrawal operation for labeled constituents of the second sample in the precolumn, and a separating operation of labeled constituents of the first sample in the separation column to be carried out in parallel or simultaneously, and wherein a liquid used for said labeling reagent, said carrier liquid, and said eluent can be selected for labeling constituents in a sample, for transferring the labeled constituents in said metering conduit to said precolumn, and for transferring labeled constituents which are withdrawn in said precolumn to said separation column, respectively, independent of one another.

2. An analytical method for analyzing a plurality of samples, which is performed by an instrument having an analytical section including, in a flow line, a metering conduit, a precolumn, a first changeover means intermediate said metering conduit and said precolumn for selectively connecting and disconnecting flow between said metering conduit and said precolumn, said first changeover means being connected to a device for providing a carrier liquid to said precolumn through the first changeover means and when said first changeover means is connecting said metering conduit and said precolumn, said carrier liquid being directed through said metering conduit for transferring a mixture in the metering conduit to the precolumn, a separation column and a detector, a second changeover means in said flow line between said precolumn and said separation column for selectively connecting and disconnecting flow between said precolumn and said separation column, said second changeover means being connected to a device for providing eluent to the separation column through the second changeover means and when said second changeover means is connecting said precolumn and said separation column said eluent being directed through the precolumn in order to transfer labeled constituents of the sample which are withdrawn in the precolumn to the separation column and a preparing section including, outside of said flow line, sample containers, a labeling reagent container, a mixing container and a pipette having a pipette nozzle, said analytical method comprising the steps:

a first step of delivering a sample from any one of the sample containers to the mixing container, delivering a labeling reagent from the labeling reagent container to the mixing container and delivering a mixture of the sample and reagent from the mixture container to an injection port of the flow line to fill the metering conduit of the analytical section with the mixture, each said delivering being performed by actuating the pipette nozzle;

a second step of transferring the mixture from the metering conduit through the flow line by way of said first changeover means to the precolumn and withdrawing labeled constituents from the mixture in said precolumn;

a third step of transferring withdrawn labeled constituents from the precolumn through the flow line by way of said second changeover means to the separation column to separate the labeled constituents and detecting the separated labeled constituents with said detector; and wherein while a first sample is subjected to said first step, a second sample, preceding the first sample, is subjected to said second step and a third sample, preceding the second sample, is subjected to said third step.

3. An analytical method according to claim 2, wherein the respective samples contain a class of catecholamines, said reagent forms the class of catecholamines into a derivative, and wherein said detector is a fluorescence detector.

4. An analytical method for analyzing a plurality of samples, which is performed by an instrument having an analytical section including, in a flow line, a metering conduit, a precolumn, a first changeover means intermediate said metering conduit and said precolumn for selectively connecting and disconnecting flow between said metering conduit and said precolumn, said first changeover means being connected to a device for providing a carrier liquid to said precolumn through the first changeover means and when said first changeover means is connecting said metering conduit and said precolumn, said carrier liquid being directed through said metering conduit for transferring a mixture in the metering conduit to the precolumn, a separation column and a detector, a second changeover means in said flow line between said precolumn and said separation column for selectively connecting and disconnecting flow between said precolumn and said separation column, said second changeover means being connected to a device for providing eluent to the separation column through the second changeover means and when said second changeover means is connecting said precolumn and said separation column said eluent being directed through the precolumn in order to transfer labeled constituents of the sample which are withdrawn in the precolumn to the separation column and a preparing section including, outside of the flow line, sample containers, a labeling reagent container, a mixing container and a single pipette having a pipette nozzle, said analytical method comprising the steps:

a first step of delivering a sample from any one of the sample containers to the mixing container, delivering a labeling reagent from the labeling reagent container to the mixing container and delivering a mixture of the sample and reagent from the mixture container to an injection port of the flow line to fill the metering conduit of the analytical section with the mixture with each delivering step being accomplished by actuating the pipette nozzle;

a second step of temporarily storing the mixture in said metering conduit and thereafter transferring the mixture temporarily stored in the metering conduit through the flow line by way of said first changeover means to the precolumn and withdrawing labeled constituents from the mixture in said precolumn; and a third step of transferring withdrawn labeled constituents from the precolumn through the flow line by way of said second changeover means to the separation column to separate the labeled constituents and detecting the separated labeled constituents with said detector; and wherein while a first sample is subjected to said first step, a second sample preceding the first sample, is subjected to said second step and a third sample, preceding the second sample, is subjected to said third step.

5. An analytical instrument for analyzing a plurality of samples, the analytical instrument comprising:

an analytical section including, in a flow line, a conduit, a precolumn, a separation column and a detector;

a preparing section including, outside of said flow line, sample containers, a labeling reagent container, a mixing container, and delivering means including a pipette having a pipette nozzle, said delivering means delivering a sample from any of the sample containers to the mixing container, delivering a labeling reagent from the labeling reagent container to the mixing container and delivering a mixture of the sample and the reagent from the mixing container to said conduit of the analytical section in said flow line, each delivering operation being accomplished by actuating said pipette nozzle;

said analytical section further including a first changeover valve in said flow line between said conduit and said precolumn for selectively connecting and disconnecting flow between said conduit and said precolumn, said first changeover valve being connected to a device for providing a carrier liquid to the precolumn through the first changeover valve and, when said first changeover valve is connecting said conduit and said precolumn, said carrier liquid being directed through the conduit for transferring the mixture in the conduit to the precolumn, and a second changeover valve in said flow line between said precolumn and said separation column for selectively connecting and disconnecting flow between said precolumn and said separation column, said second changeover valve being connected to a device for providing an eluent to the separation column through the second changeover valve and, when said second changeover valve is connecting said precolumn and said separation column said eluent being directed through the precolumn in order to transfer labeled constituents of the sample which are withdrawn in the precolumn to the separation column;

said delivering means, after finishing filling of said conduit with a mixture of a first sample and a labeling reagent from said mixing container, washing said mixing container and delivering a second sample and a labeling reagent to said mixing container with said pipette nozzle and washing said pipette nozzle before filling said conduit with the mixture of the second sample and labeling reagent; and wherein said instrument further comprises control means for controlling the first and second changeover valves and the delivering means so as to enable a mixing operation of a third sample and labeling reagent subsequent to the mixing of said second sample and labeling reagent in the preparing section, a withdrawal operation for labeled constituents of the second sample in the precolumn, and a separating operation of labeled constituents of the first sample in the separation column to be carried out in parallel or simultaneously, and wherein a liquid used for said labeling reagent, said carrier liquid, and said eluent can be selected for labeling constituents in a sample, for transferring the labeled constituents in said conduit to said precolumn, and for transferring labeled constituents which are withdrawn in said precolumn to said separation column, respectively, independent of one another.

6. An analytical instrument according to claim 5, wherein the respective samples contain a class of catecholamines, said reagent forms the class of catecholamines into a derivative, and wherein said detector is a fluorescence detector.

7. An analytical method by liquid chromatography, said method comprising steps:

reacting an introduced sample and a reagent in a reaction vessel to form a reaction liquid, trapping the reaction liquid in a precolumn to form a trap liquid, separating the trap liquid in a separation column, and detecting the separated liquid, wherein said method includes selectively changing over a sample introduction valve for said reaction liquid between a first state in which said valve is connected to a path for receiving said reaction liquid while said valve is separated from a column changeover valve for liquid, and a second state in which said sample introduction valve is connected to a transfer liquid tank and to said column changeover valve for introducing said received reaction liquid to said column changeover valve, selectively changing over said column changeover valve for liquid between a first state in which said column changeover valve is connected to the sample introduction valve for receiving liquid therefrom while said column changeover valve is connected to said precolumn, and a second state in which said column changeover valve is connected to an eluent tank and to said precolumn for introducing trap liquid from said precolumn to said separation column, and wherein a next sample and a next reagent are reacted in the reaction vessel after a preceding reaction is completed to form a next reaction liquid, and said sample introduction valve is controlled to transfer the next reaction liquid from the reaction vessel to the precolumn to form a next trap liquid, and said column changeover valve is controlled to transfer the next trap liquid from the precolumn to said separation column after a preceding separation in the separation column is completed, and wherein a liquid to be used for forming said reaction liquid, a liquid stored in said transfer liquid tank and a liquid stored in said eluent tank are selected for use in forming said reaction liquid, for transferring said reaction liquid to said precolumn, and for transferring trap liquid from said precolumn to said separation column, respectively, independent of one another.

8. A method according to claim 7, wherein a series of operations from the introduction of said sample to the detection of the separated liquid associated with said sample is divided into three steps comprising a first step including the reaction, a second step including the trap and a third step including the separation, the first, second and third steps proceeding in parallel.

* * * * *